United States Patent [19]

DeMars et al.

[11] Patent Number: 6,001,372

[45] Date of Patent: *Dec. 14, 1999

[54] ANTIGENIC PEPTIDES OF *CHLAMYDIA TRACHOMATIS*

[75] Inventors: Robert I. DeMars, Madison; Linette Ortiz, Pardeeville, both of Wis.

[73] Assignee: Wisconsin Alumni Research Foundation, Madison, Wis.

[*] Notice: This patent issued on a continued prosecution application filed under 37 CFR 1.53(d), and is subject to the twenty year patent term provisions of 35 U.S.C. 154(a)(2).

[21] Appl. No.: 08/519,385

[22] Filed: Aug. 25, 1995

[51] Int. Cl.$^6$ .......................... A61K 39/00; A61K 39/02; A61K 38/00; A61K 38/04

[52] U.S. Cl. .................... 424/263.1; 424/184.1; 424/185.1; 424/190.1; 424/234.1; 530/326; 530/328; 530/350

[58] Field of Search .............................. 424/184.1, 185.1, 424/190.1, 234.1, 263.1; 530/350, 326, 328

[56] References Cited

FOREIGN PATENT DOCUMENTS 0348725   1/1990   European Pat. Off. .......... C07K 7/08

OTHER PUBLICATIONS

Allen et al. Journal of Immunology 147(2):674–679, 1991.
Baehr et al. Proc. Natl. Acad. Sci. 85:4000–4004, 1988.
Su et al. Journal of Experimental Medicine 172:203–212, 1990.
Rank et al. Injection and Immunity 58(8): 2599–2605, 1990.
Su et al. Journal of Experimental Medicine 172: 203–212, 1990.
Zhong et al. Journal of Immunology 7(151): 3728–3736, 1993.
Peterson et al. Mol. Immunol 33(4/5) : 335–339, 1996.
E. Peterson, et al., *The Major Outer Membrane Protein Nucleotide Sequence of Chlamydia Trchomatis, Serovar E*, 18 Nucleic Acids Research, 3414 (1990).
H. Su, et al., *Identification and Characterization of T Helper Cell Epitopes of The Major Outer Membrane Protein of Chlamydia Trachomatis*, 172 J. Experim. Med. 203–212 (1990).
J. Allen, et al., *A Single Peptide From The Major Outer Membrane Protein of Chlamydia Trachomatis Elicits T Cell Help For The Production of Antibodies To Protective Determinants*, 147 J. Immunol. 674–679 (1991).

M. Ishizaki, et al., *Immune Specificity of Murine T–Cell Lines To The Major Outer Membrane Protein Of Chlamydia Trachomatis*, 60 Infection and Immunity, 3714–3718 (1992).
H. Su, et al., *Immunogenicity Of A Chimeric Peptide Corresponding To T Helper And B Cell Epitopes Of The Chlamydia Trachomatis Major Outer Membrane Protein*, 178 J. Experim. Med. 227–235 (1992).
G. Zhong, et al., *Immunogenicity Evaluation Of A Lipidic Amino Acid–Based Synthetic Peptide Vaccine For Chlamydia Trachomatis*, 151 J. Immuno. 3728–3736 (1993).
A. Stagg, et al., *Primary Human T–cell Responses To The Major Outer Membrane Protein Of Chlamydia Trachomatis*, 79 Immunology 1–9 (1993).
P. Kavathas, et al., *Gamma Ray–Induced loss Of Expression Of HLA And Glyoxalase I Alleles In Lymphoblastoid Cells*, 77 Proc. Nat. Acad. Sci. USA 4251–4255 (1980).
R. DeMars, et al., *Homozygous Deletions That Simultaneously Eliminate Expression Of Class I and Class II Antigens of EBV–Transformed B–Lymphoblastoid Cells. I. Reduced Proliferative Responses of Autologous And Allogeneic T Cells to Mutant Cells That Have Decreased Expression Of Class II Antigens*, 11 Hum. Immuno. 77–97 (1984).
R. DeMars, et al., *Dissection Of The D–Region Of The Human Major Histocompatibility Complex By Means Of Induced Mutations In a Lymphoblastoid Cell Line*, 8 Hum. Immunol. 123–139 (1983).
S. Ceman, et al., *MHC Class II Deletion Mutant Expresses Normal Levels Of Trangene Encoded Class II Molecules That Have Abnormal Conformation And Impaired Antigen Presentation Ability*, 149 J. Immuno. 754–761 (1992).
S. Ceman, et al., *DMA And DMB Art The Only Genes In The Class II Region Of The Human MHC Needed For Class II–Associated Antigen Processing*, 154 J. Immunol. 2545–2556 (1995).
F. Schödel, et al., *Hybrid Hepatitis B Virus Core–Pre S Proteins Synthesized In Avirulent Salmonella Typhimurium and Salmonella Typhi for Oral Vaccination*, 62 Infec. Immunol. 1669–1676 (1994).

*Primary Examiner*—James C. Housel
*Assistant Examiner*—V. Ryan
*Attorney, Agent, or Firm*—Quarles & Brady LLP

[57] ABSTRACT

Disclosed herein are short antigenic peptides of MOMP protein from *Chlamydia trachomatis*. They can be used to stimulate antigenic responses and to diagnose the presence of the bacteria.

1 Claim, No Drawings

ANTIGENIC PEPTIDES OF *CHLAMYDIA TRACHOMATIS*

STATEMENT REGARDING FEDERALLY SPONSORED RESEARCH

This invention was made with Unites States government support awarded by NIH grant #'s RO1AI15486-17 T and PO1AI34617-2. The United States Government has certain rights in this invention.

TECHNICAL FIELD

The present invention relates to antigenic peptide fragments of the major outer membrane protein ("MOMP") from *Chlamydia trachomatis*. These peptides appear to be especially well suited for use in detecting the presence of blood lymphocytes that specifically recognize these bacteria (as an indicator of prior infection) and for provoking immune responses to MOMP.

BACKGROUND OF THE ART

*Chlamydia trachomatis* ("CT") is an intracellular bacteria that is the leading cause of preventable infectious blindness (ocular trachoma) in the developing world and of sexually transmitted disease ("STD") in the United States and certain other parts of the developed world. The estimated annual incidence of CT-caused STD is in the millions. While most CT caused disease can be treated with antibiotics, untreated or inadequately treated infections result in hundreds of thousands of cases of pelvic inflammatory disease each year in the United States, alone. Adverse outcomes of pregnancy, ectopic pregnancy and tubal infertility are among the consequences. Moreover, apparent clearance of infection by a given serovar (serologically distinct strain of CT) can be followed by the infection becoming latent and prolonged or by re-infection. This is important because much CT-caused pathology results from tissue-damaging inflammatory responses of the immune system that are triggered by repeated or prolonged exposures to the whole organism. Therefore, there is a need for: (i) means to detect signs of prior or of persistent covert infection in individuals who have pelvic inflammatory disease or its sequelae listed above; and (ii) means to prevent primary and repeat infections.

Thus, means have been sought to test for CT in humans, to monitor the effectiveness of antibiotic treatment, and to detect signs of covert infection. Means have also been sought to manipulate the immune system (e.g. by vaccination) to prevent CT infections.

Some tests to determine the presence of CT already exist. For example, some DNA hybridization probe tests are known. However, these tests are not well suited to detecting evidence of tissue-damaging immune responses once the number of live organisms becomes small, as in many individuals with CT-caused pathologies.

With respect to vaccines, intact killed bacteria have been tried in human volunteers, but without success (pathological side effects/inadequate protection). The art is also aware that antibody responses are directed at the surface-exposed MOMP of CT. Thus, MOMP has been a focus of vaccine-based research for some time.

Sequence analysis of MOMP has revealed that amino acid sequence variation between serovar isolates accounts for the antigenic diversity of this pathogen. See E. Peterson et al., 18 Nuc. Acids. Res. 3414 (1990) (nucleotide sequence of serovar E) and M. Ishizaki et al., 60 Infect. & Immun. 3714–3718 (1992). The disclosure of these publications, and of all other publications referred herein, are incorporated by reference as if fully set forth herein.

Unfortunately, whole MOMP is too difficult to isolate from natural CT cultures in large quantities that are sufficiently pure for use in mass vaccination. Larger quantities of recombinant MOMP could theoretically be produced in *E. coli*, but the chemical properties (e.g. insolubility except in detergents) impede its large scale preparation as a non-toxic vaccine. In any event, use of whole MOMP has too much risk of adverse side effects.

Attempts have therefore been made to develop vaccines based on MOMP fragments. For example, papers have been published describing use of certain peptide fragments of MOMP to raise antigenic responses to certain serovars (A,B,C) in mice. See e.g. H.Su et al., 172 J. Exp. Med. 203–212 (1990) (serovar A); J. Allen et al., 147 J. Immunol. 674–679 (1991) (serovar B); M.Ishizaki et al., 60 Infect. & Immun. 3714–3718 (1992) (serovars B, C); G.Zhong et al., 151 J. Immunol. 3728–3736 (1993) (serovar B).

However, the value of these studies in mouse in identifying potential vaccine components for humans is now known to be very limited. Only one MOMP epitope to which mouse lymphocytes respond may correspond to one of at least nine epitopes that we have found to activate human T lymphocytes. Also, antigenic MOMP fragments identified in these murine experiments even had limited predictive value among mice. In this regard, fragments recognized by the lymphocytes of one strain were often not recognized by other mouse strains.

A. Stagg et al., 79 Immunol. 1–9 (1993) attempted to locate antigenic fragments in serovar L in human cell experiments. They exposed, in vitro, T-cells from naive individuals to five peptides and looked for proliferation responses. They identified a strong antigenic region "213–224" partially overlapping a variable (serovar specific region of serovar L), as well as several weakly antigenic fragments "116–127", "135–146" and "274–285".

Apart from serovar specificity issues, humans have a variety of MHC class II types, each type determining the specific antigenic groups to which an individual's immune system can respond. Thus, what is antigenic for one human MHC type, may not be antigenic for others. This is a particularly troubling problem for those seeking to develop vaccines for the human population in general.

As such, a need exists for short antigenic MOMP fragments that are present in most or all *Chlamydia trachomatis* serovars and also are recognized by most human MHC types.

DISCLOSURE OF THE INVENTION

In one aspect, the invention provides a peptide having in it at least eight (preferably at least nine, ten or eleven) consecutive amino acid residues that are also present consecutively in either SEQ ID NO. 1 or NO. 2. The peptide has no sequence with greater than 39 consecutive amino acid residues from MOMP *Chlamydia trachomatis* serovar E (optionally none greater than 24), and preferably includes the whole SEQ ID NO. 1 or 2.

In another respect, the invention provides recombinant nucleotide sequences capable of expressing the above peptides.

The objects of the present invention therefore include providing peptides of the above kind which:

(a) stimulate an antigenic response in most humans;

(b) are present in most *Chlamydia trachomatis* serovars;

(c) are short enough to minimize the risk of side effects and can be produced efficiently; and (d) which are suitable for use in diagnostic tests and/or vaccines.

Another object of the present invention is to provide nucleotides sequences capable of expressing the above peptides either in vivo (in the case of a vaccine), or in vitro (as a recombinant source of the protein).

These and still other objects and advantages of the present invention will be apparent from the description which follows. The following description merely contains examples of the present invention. The claims should therefore be looked to in order to appreciate the full scope of the invention.

BEST MODES FOR CARRYING OUT THE INVENTION

Overall Approach

We divided the known 393 amino acid MOMP protein from *Chlamydia trachomatis* serovar E into six fractions of about seventy amino acid residues each (M1/6 through M6/6), each of which was produced recombinantly. Some of these fractions stimulated proliferation in vitro of T cells obtained from CT-infected people. We then designed overlapping peptides of approximately twenty amino acids to cover the length of the active fractions looking for antigenic peptides in "constant" regions. The MOMP protein consists of five "constant" regions and four variable ones. The amino acid sequences of "constant" regions are substantially conserved from serovar to serovar.

The overlapping conserved peptides were tested in vitro for their ability to cause T-cell proliferation. Importantly, the proliferation studies were performed on cultures from diseased humans, not naive ones. These assisted in permitting identification of segments that are not only antigenic, but also widely antigenic across the tested human population.

Moreover, we also needed to develop ways to find which types of MHC class II molecules were responsible for presenting peptides of this type to the immune system as a means of determining which short peptide combinations were optimum, based on the frequencies of those MHC class II types in the relevant population. Note in this regard that there are three main categories of class II molecules (see below), and that most people can form at least two kinds of each category. Therefore, most people have six types of MHC class II molecules available. There are also numerous sub-types of class II molecules.

The three main kinds of MHC class II molecules are HLA-DP, -DQ and -DR. Each kind of class II molecule consists of an alpha and beta chain that are encoded by separate genes and that are associated in a way that permits it to bind a peptide in a groove that can then be displayed outside the cell once the class II-peptide complex becomes anchored at the cell surface. Most humans are heterozygous for alleles of the DP and DQ alpha and beta genes and for the DR beta gene (only one DR alpha allele is known). Since many different possible alpha-beta combinations of a given kind of class II molecule can form, individual cells of a person can sometimes express as many as four kinds of DP molecules, four kinds of DQ molecules and two kinds of DR molecules.

To try to determine which peptides are antigenic for a wide range of humans, we first used monoclonal antibodies that bind specifically to either DP, DQ or DR. We have shown that the proliferative responses of cells that recognize MOMP-derived antigenic peptides associated with a specific kind of class II molecule are almost completely blocked in the presence of a monoclonal antibody that binds to that kind of class II molecule. This approach is useful to identify the category of class II molecule to which the peptide binds in some situations, but is limited by the low availability of antibodies that bind to certain specific different allelic products of DP, DQ and DR.

We therefore also use antigenic presenting cells ("APC") which are Epstein-Barr virus-transformed human B lymphoblastoid cell lines ("LCL") that have specific mutations that we made in the major histocompatibility complex or that expressed just one kind or another of cloned MHC class II molecule as a result of gene transfer. The specific loss of or acquired expression of specific MHC class II molecules in these lines made possible unambiguous determination of the function of the affected class II molecules as elements for use with the specific MOMP fragments.

Our test cells would not respond to MOMP or to antigenic parts of MOMP unless the APC presents the antigenic peptides in association with a kind of class II molecule that is also encoded in the T cells. We used this to zero in on the identities of class II molecules that present antigenic parts of MOMP by quantifying proliferation of a given MOMP primed T-population in response to antigen presented by a collection of LCL-APC that match one or another class II allele present in the T cells.

For example, APC "STD15" could have formed seven kinds of class II molecules, i.e. two kinds of DR alpha-beta combinations, four kinds of DQ alpha-beta combinations and one kind of DP alpha-beta combination. The possible identities were narrowed by the use of our mutant APC .114, which can form only one kind of DR, DQ and DP molecule, each of which matches one pair of class II alpha and beta alleles present in the T-MOMP cells.

Creation of modifications of MHC are generally described in P. Kavathas et al., 77 Proc. Nat. Acad. Sci. USA 4251–4255 (1980) (procedures for mutagenesis and isolation of MHC mutant LCLs); R. DeMars et al., 8 Hum. Immunol. 123–139 (1983) (origin of LCL mutant .114); R. DeMars et al., 11 Hum. Immunol. 77–97 (1984) (origin of LCL mutant .174, see below); S. Ceman et al., 149 J. Immunol. 754–761 (1992) (describes use of gene transfer to restore class II expression to mutant .174, but antigen presentation function not restored); S. Ceman et al., 154 J. Immunol. 2545–2556 (1995) (use of transfer of DM genes into .174 to restore ability of cells to load antigenic peptides onto the class II molecules they express). APC Mutant .114 was created by mutagenesis that eliminated from an "ordinary" heterozygous LCL one complete copy of the MHC, in which all of the class II genes are located. However, use of APC .114 still left three possible kinds of class II molecules for presenting antigenic parts of MOMP.

Use of HLA-DR17 (i.e. DR alpha+DR beta 0301) to present MOMP antigenic "epitopes" from among the three possibilities in APC .114 was then demonstrated with the use of another kind of LCL-APC, Transferent .174 (DR17). This cell line was made by mutagenically deleting all class II genes from an LCL. We then sequentially added back cloned genes for DR alpha and for DM alpha and DR beta. The DM genes are needed in order to load peptides onto class II molecules. The resultant cell line has been used as the recipient of diverse cloned DR beta genes, resulting in the production of a growing collection of LCL APCs, each of which expresses just one kind or another of DR molecule. Stimulation of T cell proliferation by a Transferent expressing a given kind of DR molecule directly identifies that kind of DR as one that presents a MOMP epitope to T-MOMP' cells. 174 (DR17) elicited proliferation of STD15 T cells primed in the presence of MOMP in excess of that observed in the absence of antigen or in the presence of a control antigen, tetanus toxoid.

T lymphocytes that responded specifically to antigenic MOMP CT were prepared by starting with a sample (about 30 ml) of venous blood from human subjects who have had symptomatic and confirmed CT infections within six months preceding and up to the time of blood sampling. The cells were "primed" by culturing them in vitro for about 7 days in a medium containing MOMP purified from CT organisms. Proliferation of T cells that are specifically activated by the MOMP was then "driven" by addition of IL-2 for an additional week. The resultant driven cell populations were named T-MOMP'.

T-MOMP' cells proliferated in specific response to MOMP and not to other tested control antigens, such as tetanus toxoid, to which the same individuals are shown to respond. For instance, when T cells from the same individuals were primed with tetanus toxoid instead of MOMP, the resultant T cell population proliferated in specific response to tetanus toxoid and not at all in response to MOMP.

These results are evidence of two important things: (i) almost every adult in the U.S. has been vaccinated with tetanus toxoid and has "memory" cells that respond to the toxoid by proliferating. Thus, we were able to greatly increase the numbers of these cells in toxoid-containing cultures of T cells derived from our STD subjects. But tet-tox-primed T cells did not respond to MOMP.

In addition, we have shown that individuals who have had verified CT infections also have memory T cells that respond to MOMP. These cells are present because the immune systems of the infected individuals processed MOMP from the living organisms into antigenic parts ("epitopes") that stimulated the establishment of a "bank" of T memory cells that could subsequently respond to the epitopes. We showed this by stimulating outgrowth of the cells by culturing them in the presence of MOMP and of MOMP peptides.

Results

T cells from CT infected individuals responded strongly to SEQ ID NO. 1 and 2 (peptides 243–273 and 89–105 of the serovar E sequence). Epitopes in these peptides were narrowly located by testing proliferative T cell responses to overlapping 11–13 mers or other overlapping peptides. For example, we discovered that sub-fragments of SEQ ID. NO: 1 were highly antigenic (e.g. 243–257; 249–265; 253–265; 260–273). The shorter active peptides were tested with T-MOMP' cells from individuals having different kinds of class II molecules by using LCL antigen-presenting cells that had class II molecules to match those on the T-MOMP' cells.

As an example, we found that the .174 (DR17) Transferent APC not only binds and presents peptide 249–265, but also the fragment 253–265. Stimulation of T cells by the epitope present in peptide presented by HLA-DR17 strongly depends on the presence of amino acid residue 264 or 265 (or both).

But when the same peptides were tested using LCL APCs expressing other kinds of DR and with T-MOMP' cells containing those DR alleles, each DR type gave a characteristic pattern of stimulatory and non-stimulatory peptides in the 249–265 serovar E sequence.

Overall, our research indicates that at least these MOMP T cells epitopes exist: at least one is 243–257; at least three in 249–265; at least one in 260–273. These epitopes are presented with at least HLA-DR7, DR8, DR13, DR14, DR17, DR18. In the population of 37 CT-infected subjects of the above studies, 92 percent of the subjects had at least one of the listed DR alleles. To improve the coverage still further, we suggest simultaneous use of 89–105.

Importantly, SEQ ID NOs. 1 and 2 are entirely within the MOMP "constant" segments CS2 and CS4 found in known *Chlamydia trachomatis* serovars. Moreover they can be efficiently synthetically created using Fmoc chemistry (described in G. A. Grant *Synthetic Peptides. A User's Guide.*, W. H. Freeman and Co. (1992) and available automatic peptide synthesizers (e.g. we used the model 432A "Synergy" apparatus supplied by Applied Biosystems Division of Perkin Elmer Cetus), or expressed recombinantly using nucleotide information from Peterson, et al. supra for the nucleotide sequences corresponding to the amino acid residues.

Polynucleotides encoding the sequences will be synthesized by means of the polymerase chain reaction (see M. A. Innis et al., editors *PCR Protocols, A Guide to Methods and Applications,* John Wiley & Sons (1993).

Diagnostic Use

A diagnostic test is intended for use in: (a) diagnosing MOMP epitope-specific T cells in individuals who have or may be at risk of developing pelvic inflammatory disease or its complications; and (b) monitoring T cells responses of humans to whom MOMP or MOMP peptide vaccines are administered.

Peripheral blood mononuclear cells (PMBC) from patients suspected to have been infected are prepared from 5–10 ml of heparinized venous blood from humans. The blood sample (drawn within 48 hr prior to setting up the test) is diluted with an equal volume of phosphate buffered saline (PBS) and is layered over 15 ml of Ficol-Hypaque in a 50 ml conical centrifuge tube and the tube is spun in an "ordinary" (e.g. table-top) centrifuge at 500×g for 30 minutes. The cells forming a thin layer at the Ficoll-upper aqueous layers are collected with a pipette, are washed twice with PBS and are resuspended at $10^6$ cells per ml in "HS" culture medium consisting of RPMI 1640 (90 v) plus pooled human AB negative serum (10 v).

APC automatically are present in the PBMC fraction isolated above. Thus, no immortalized APC needs to be separately added for this purpose.

The preferred MOMP peptides are SEQ ID NO. 1 (corresponding to 243–273) and SEQ ID NO. 2 (corresponding to 89–105) in equal amounts (with or without amino acid peptides 206–225, and/or 271–287). Each peptide is dissolved individually at 2 mg/ml in dimethyl disulfoxide (DMSO) or as a mixture containing each at 2 mg/ml.

Samples (190 μl) of PBMC suspension from an individual are distributed into wells of microtiter plates. Aliquots of each peptide solution are then added to the microtiter wells. One set of wells receive 10 μl aliquots of the solution containing a mixture of the peptides, while another set of wells receive 10 μl of HS medium as a no-antigen control. The plates are incubated in a humidified 5% $CO_2$ incubator at 37° for 48 hr. The wells then receive 50 μl of HS medium containing 1 μC tritiated thymidine (ie. $^3$H-Tdr, about 2 Ci/mmole specific activity) and incubation is continued.

T cells respond by proliferating and incorporate $^3$H-Tdr into the DNA they are synthesizing. T cells that do not recognize the peptide do not proliferate (and thus do not incorporate $^3$H-Tdr). After about a 15 hr interval for $^3$H-Tdr incorporation the cells are harvested with a "MASH" device, are washed three times with water and deposited on small fiberglass discs (8 mm diameter). The discs are dried in air and are placed in small vials containing scintillation counting fluid (e.g. Bio-Safe II). The incorporated radioactivity in the cells deposited on each disc is then quantified with a standard liquid scintillation counter.

Each antigen condition is tested in triplicate with PBMC from any one individual. The mean value of the without-antigen control ("background") is subtracted from the mean incorporated counts per minute (CPM) for each triplicate. Increments of cpm significantly above background indicate response to an antigen, and hence an individual that has made an immune response to CT infection or can do so.

Vaccine Protocol—A

In sterile dropper bottle the suspending medium is sterile phosphate-buffered saline. The synthetic peptides are SEQ ID NO. 1 and NO. 2 (optionally with serovar E amino acid residues such as 206–225 and 271–287). Each peptide is at 4 mg/ml. Cholera toxin subunit B at 2 mg/ml is also present to enhance immune responses at mucosal surfaces, which are the sites at which CT multiply and cause pathology. Use of subunit B has been safely tested with humans in other contexts.

To administer to a human, one shakes well, and uses two drops (about 0.1 ml) in each nostril and each eye. Administration should preferably be on days 0, 7 and 14. B cell epitope peptides may also optionally be included, as may booster applications. Peptides bearing these epitopes could directly activate B cells that recognize the epitopes and the proliferation of these B cells would be enhanced by growth-stimulating interleukins secreted by the T cells responding to the T epitopes in the vaccine.

Vaccine Protocol—B

The proposed vaccine agent is an attenuated bacterial strain of *Salmonella typhimurium* bearing a replicating plasmid into which is inserted DNA sequences capable of expressing the peptides of interest in vivo. We propose as a vector attenuated *Salmonella typhimurium* strain $_x$4072. See F. Schödel et al., 62 Infect. and Immun. 1669–1676 (1994) which has Δ crp-1 and Δ cya mutations that render it avirulent and a Δ asdA-1 mutation that renders it inviable unless a normal asdA gene is present on an indwelling plasmid.

Plasmid PYAN is a form of pYA292 that is modified to have a Nco I site. See Schödel et al., supra. The presence of the Nco I site allows in frame insertion of the AUG of the foreign protein of interest into the plasmid. pYAN lacks antibiotic resistance genes, allowing use of antibiotics should symptoms suggestive of Salmonella pathology appear.

pYAN does have a normal asdA gene, which maintains viability of only those bacteria that retain the plasmid. A DNA sequence is synthesized encoding an AUG followed by the sequences encoding MOMP amino acid sequences 89–105 and 243–273 with a few (e.g. 3) amino acids intervening between each epitope bearing segment. The suggested dose is $5 \times 10^4$ colony forming units for small children and $5 \times 10^5$ colony forming units for adults.

For adults, the bacteria will be administered with sodium bicarbonate (2 g of NaHCO in 150 ml of distilled water). One should first drink 120 ml of the solution to neutralize gastric acid. One minute later, one drinks the remaining 30 ml of bicarbonate solution, now containing the bacteria. No food or drink is permitted for 90 minutes before or after vaccination.

Industrial Applicability

This invention is useful in testing for possible deleterious immune responses to *Chlamydia trachomatis* infections in humans and for creating and monitoring protective immune responses to the organism in humans.

SEQUENCE LISTING (1) GENERAL INFORMATION:

(iii) NUMBER OF SEQUENCES:2

(2) INFORMATION FOR SEQ ID NO:1:

(i) SEQUENCE CHARACTERISTICS:
      (A) LENGTH:  31 amino acids
      (B) TYPE:  amino acid
      (C) STRANDEDNESS:  single
      (D) TOPOLOGY:  linear (ii) MOLECULE TYPE:  peptide (iii) HYPOTHETICAL:  no (iv) ANTI-SENSE:  no (v) FRAGMENT TYPE:  internal fragment (vi) ORIGINAL SOURCE:
      (A) ORGANISM:  Chlamydia trachomatis
      (B) STRAIN:  Serovar E
      (C) INDIVIDUAL ISOLATE:  MOMP Protein (xi) SEQUENCE DESCRIPTION:  SEQ ID NO:1:

SER ILE ASP TRP HIS GLU TRP GLN ALA SER LEU ALA LEU SER TYR ARG
1               5                  10                  15

```
LEU ASN MET PHE THR PRO TYR ILE GLY VAL LYS TRP SER ARG ALA
        20                  25                  30

(2) INFORMATION FOR SEQ ID NO:2:

(i) SEQUENCE CHARACTERISTICS:
        (A) LENGTH:  17 amino acids
        (B) TYPE:  amino acid
        (C) STRANDEDNESS:  single
        (D) TOPOLOGY:  linear (ii) MOLECULE TYPE:  peptide (iii) HYPOTHETICAL:  no (iv) ANTI-SENSE:  no (v) FRAGMENT TYPE:  internal fragment (vi) ORIGINAL SOURCE:
        (A) ORGANISM:  Chlamydia trachomatis
        (B) STRAIN:  Serovar E
        (C) INDIVIDUAL ISOLATE:  MOMP Protein (xi) SEQUENCE DESCRIPTION:  SEQ ID NO:2:

ARG HIS MET GLN ASP ALA GLU MET PHE THR ASN ALA ALA CYS MET ALA
1               5                  10                  15

LEU
```

We claim:

1. A peptide containing a human T cell epitope, the peptide being selected from the group consisting of:
   (a) a peptide consisting of a sequence of consecutive amino acid residues which is SEQ ID NO. 1 residues 7–23; and
   (b) a peptide consisting of a sequence of consecutive amino acid residues which is SEQ ID NO. 2 residues 1–17.

* * * * *